(12) United States Patent  (10) Patent No.: US 8,394,961 B2
Jirman et al.  (45) Date of Patent: Mar. 12, 2013

(54) METHOD FOR THE PREPARATION OF DABIGATRAN

(75) Inventors: Josef Jirman, Praha (CZ); Jindrich Richter, Pardubice (CZ); Petr Lustig, Pardubice (CZ)

(73) Assignee: Zentiva k.s., Praha (CZ)

( * ) Notice: Subject to any disclaimer, the term of this patent is extended or adjusted under 35 U.S.C. 154(b) by 212 days.

(21) Appl. No.: 12/922,214

(22) PCT Filed: Mar. 10, 2009

(86) PCT No.: PCT/CZ2009/000037
§ 371 (c)(1),
(2), (4) Date: Dec. 6, 2010

(87) PCT Pub. No.: WO2009/111997
PCT Pub. Date: Sep. 17, 2009

(65) Prior Publication Data
US 2011/0082299 A1  Apr. 7, 2011

(30) Foreign Application Priority Data

Mar. 14, 2008 (CZ) ................................. 2008-165

(51) Int. Cl.
*C07D 401/12* (2006.01)
(52) U.S. Cl. .................................................. 546/273.4
(58) Field of Classification Search ............... 546/273.4
See application file for complete search history.

(56) References Cited

FOREIGN PATENT DOCUMENTS

WO   WO 98/37075     8/1998
WO   WO 2006/000353  1/2006
WO   WO 2007/071742  6/2007

OTHER PUBLICATIONS

International Search Report, for International application PCT/CZ2009/000037, Date of Mailing: Jun. 10, 2009.
Hauel et al, Structure-Based Design of Novel Potent Nonpeptide Thrombin Inhibitors, J. Med. Chem, 2002, 45, pp. 1757-1766.

*Primary Examiner* — Patricia L Morris
(74) *Attorney, Agent, or Firm* — Pearl Cohen Zedek Latzer, LLP

(57) ABSTRACT

A method for the manufacture of dabigatran of formula VIII, in which the product of a reaction of 4-ethylamino-3-nitrobenzoic acid chloride with ethyl-3-(pyridin-2-ylamino) propanoate, is converted to the hydrochloride using a hydrogen chloride solution producing the compound of formula III-HCl, in which the nitro group is reduced by means of a reaction with sodium dithionite, and the resulting compound of formula IV is subjected to a reaction with [(4-cyanophenyl)amino]acetic acid and oxalic acid, the product of this reaction VI-oxal is then subjected to hydrolysis and a reaction with ammonium carbonate to produce the intermediate of formula VII-HCl, which is then converted to dabigatran by means of a reaction with hexyl chloroformate.

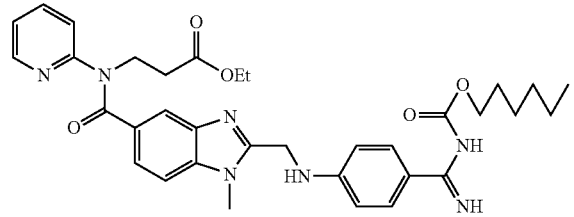

VIII

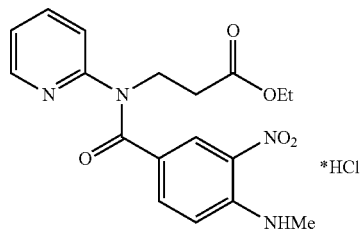

III-HCl

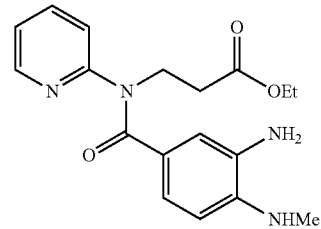

IV

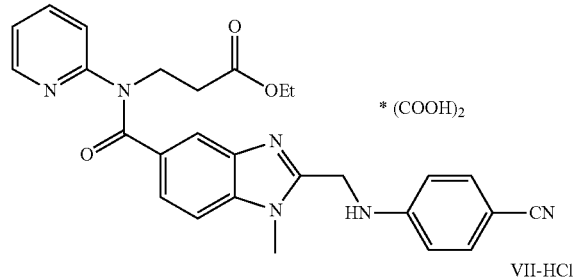

VI-oxal

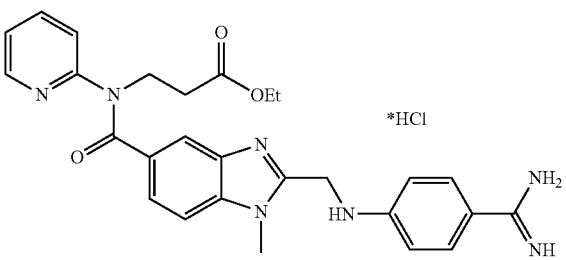

VII-HCl

18 Claims, No Drawings

METHOD FOR THE PREPARATION OF DABIGATRAN

This application is a National Phase Application of PCT International Application No. PCT/CZ2009/000037, International Filing Date Mar. 10, 2009, entitled "A METHOD FOR THE PREPARATION OF DABIGATRAN", published on Sep. 17, 2009 as International Publication Number WO 2009/111997, which claims priority of Czech Patent application No. PV 2008-165, filed Mar. 14, 2008, both of which are incorporated herein by reference in their entirety.

TECHNICAL FIELD

The invention relates to a new method for the manufacture of 3-([2-[[(4-(N-n-hexyloxycarbonylcarbamimidoyl)-phenylamino]-methyl]]-1-methyl-1H-benzimidazole-5-carbonyl]-pyridin-2-yl-amino)ethyl propionate, known under the international non-proprietary name dabigatran.

Dabigatran is an anticoagulant compound and it is used for treatment of thromboses, cardiovascular diseases, and the like.

BACKGROUND ART

The substance was first described in the document WO 9837075. Its preparation procedure in accordance with the above mentioned document is shown in Scheme 1.

In the first production stage the chloride of compound I reacts with compound II in tetrahydrofuran using triethylamine as a base. Substance III is the product of the reaction. During a reproduction of the above mentioned procedure substance III was obtained in the base form. However, in our experience and in accordance with WO 9837075 this substance requires complex purifying operations, e.g. chromatography, in order to be used for the production of high-quality API.

The next production stage is reduction of the nitro group to the amino group. In the document WO 9837075 this reaction is performed by means of catalytic hydrogenation with the use of palladium on active carbon under high pressure. However, this process has very high technological demands and manifests safety and environmental risks. It requires the use of high pressure and therefore special equipment is necessary. The catalysts used are toxic and their price together with the price of the equipment is very negatively reflected in the economy of the whole process. Another disadvantage of this process is a very low quality of the product of formula IV obtained this way. This way the product is obtained in an oily form with the content of impurities of 20-40%. Product IV, at least according to the known process, must enter the next stage in a contaminated form. Finding an alternative method of performing this reaction would certainly represent a great contribution to making the production of dabigatran more efficient.

In the third stage substance IV reacts with substance V, producing substance VI. According to WO 9837075 compound V is prepared by a reaction of 4-cyanophenyl aniline with chloroacetic acid in the presence of a base. During a reproduction of the procedure of WO 9837075 we found out that the reaction provides a low yield (about 50%). The product of the procedure in accordance with WO 9837075 is compound VI in the base or acetate form. Both these products require chromatographic purification, which is very difficult to implement in the industrial scale.

In the next stage acidic hydrolysis of the nitrile function of compound VI and reaction with ammonium carbonate producing compound VII is carried out. The last stage is a reaction of intermediate VII with hexyl chloroformate producing dabigatran.

Scheme 1. Procedure for the preparation of dabigatran according to WO 9837075

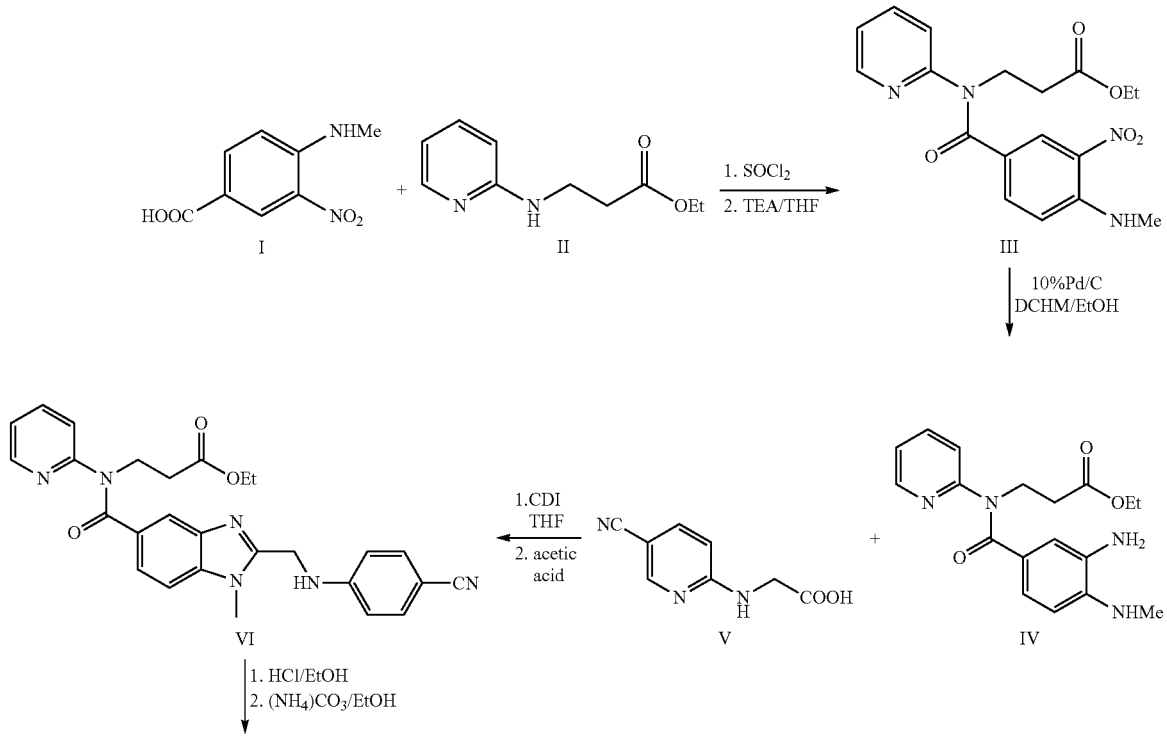

-continued
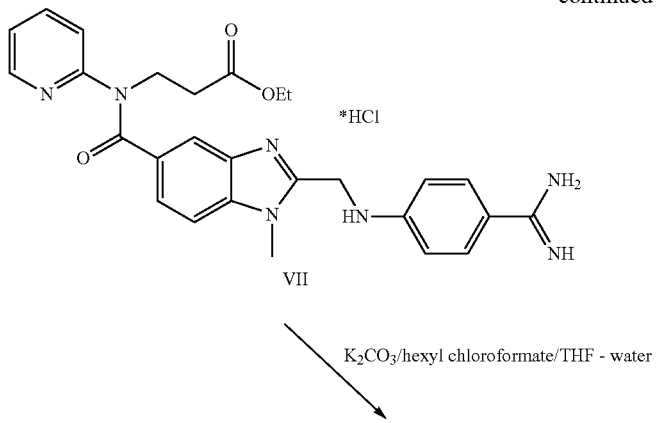
VII
K₂CO₃/hexyl chloroformate/THF - water
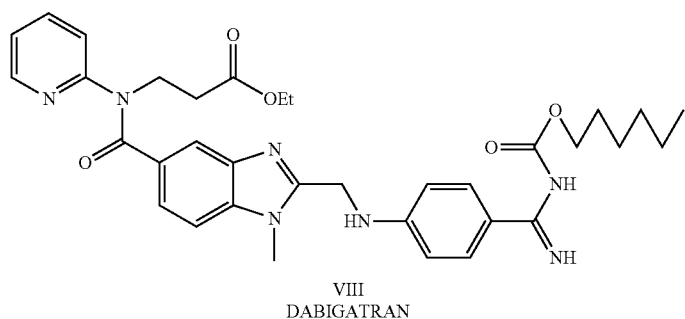
VIII
DABIGATRAN
DISCLOSURE OF INVENTION
The invention deals with a new method for the manufacture of 3-([2-[[(4-(N-n-hexyloxycarbonylcarbamimidoyl)phenylamino]-methyl]]-1-methyl-1H-benzimidazole-5-carbonyl]-pyridin-2-yl-amino)ethyl propionate of formula VIII
VIII
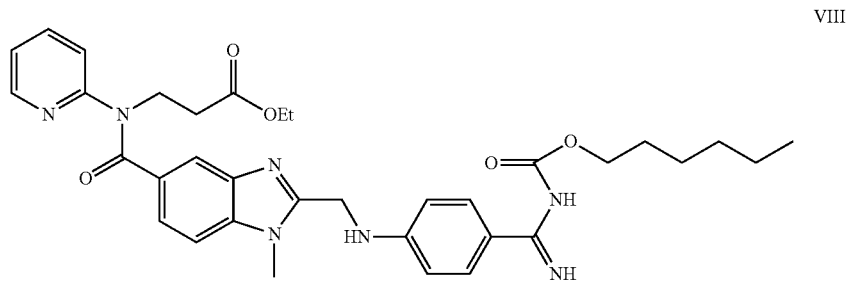 [SMILES: CCCCCCOC(=O)NC(=N)c1ccc(NCc2nc3cc(C(=O)N(CCC(=O)OCC)c4ccccn4)ccc3n2C)cc1]

known under the international non-proprietary name dabigatran. Dabigatran is an anticoagulant compound and is used for the treatment of thromboses, cardiovascular diseases, and the like.
The procedure according to the present invention is shown in Scheme 2.
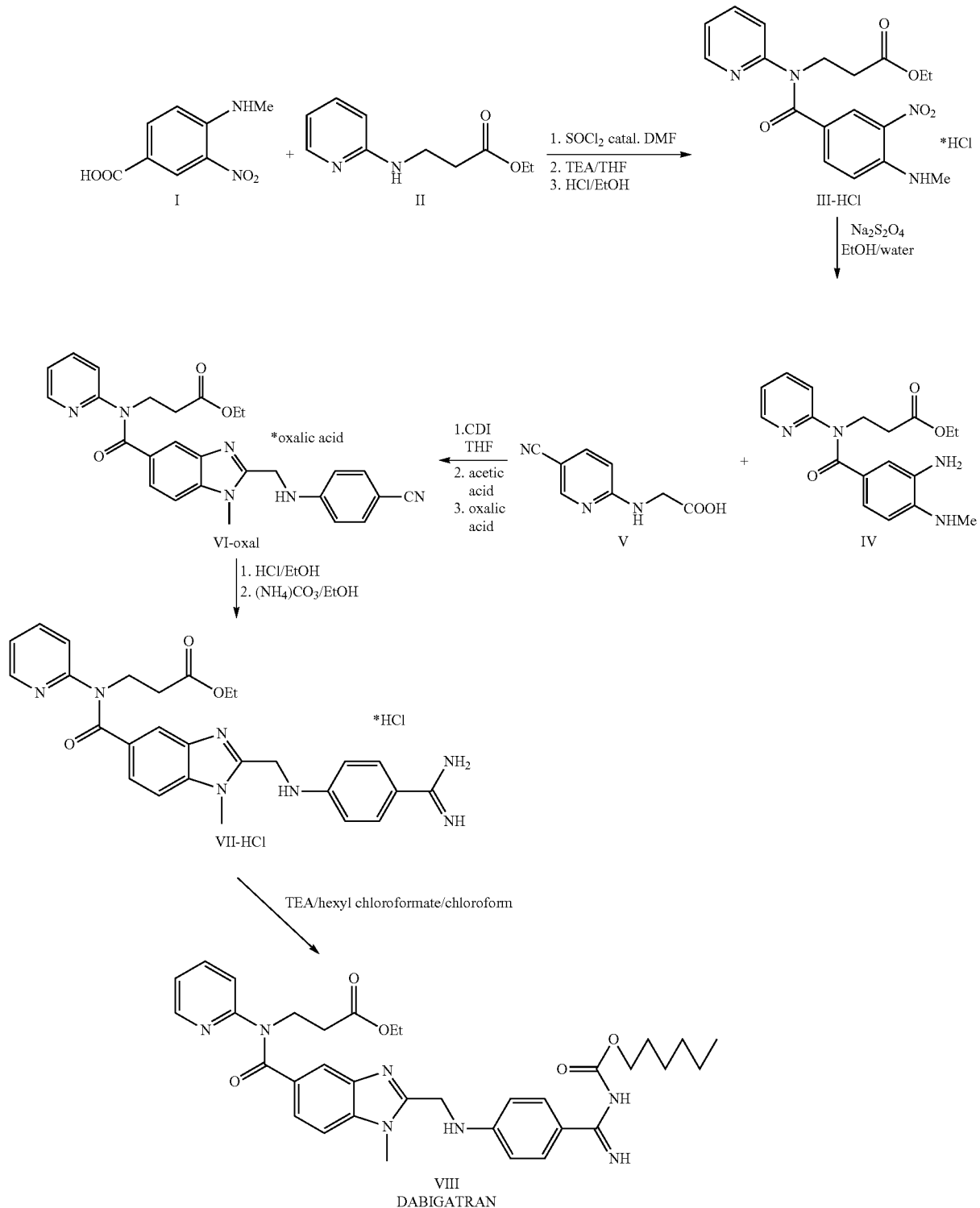
Scheme 2. Procedure for the preparation of dabigatran according to the present invention In the first stage the chloride of compound I reacts with compound II in tetrahydrofuran in the presence of a base. The base used is selected from amines, alcoholates, hydroxides, phosphates and carbonates. Triethylamine appears to be the most suitable base.

The procedure according to the present invention after the reaction with a solution of hydrogen chloride in an organic solvent produces compound III in the hydrochloride form. This substance can be re-purified by simple crystallization, e.g. from the ethanol acetonitrile mixture, which leads to a high-purity product, often with a content of impurities lower than 1%, e.g. with the content of the desired substance of 99.3%.

Hydrogen chloride is dissolved in an organic solvent selected, e.g., from the group of ethers, esters, ketones and alcohols. Diethylether appears to be the most suitable one. The next production stage is reduction of the nitro group to the amino group.

The procedure according to the present invention is performed in a solvent mixture of ethanol and water. The reagent is sodium dithionite. It is not necessary to operate at elevated pressure or very high temperature. This procedure is much less costly and more advantageous from the economic point of view. Substance III enters the reaction in the hydrochloride form, which has a positive influence on the course of the reaction and purity of the product. Using the combination of changing the quality and composition of the starting substance and of the method of reduction of the nitro group it is possible to obtain product IV with a minimum content of impurities, i.e. less that 5%, preferably less than 1%.

In stage three substance IV reacts with the substance of formula V producing the compound of formula VI.

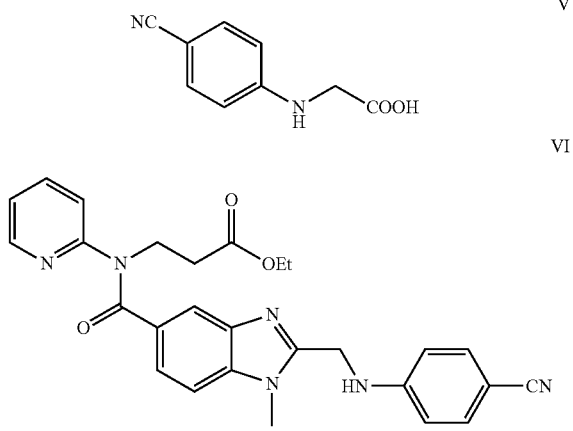

Within the procedure based on the present invention compound VI is obtained in the form of a salt with oxalic acid. This salt is simply re-purified by further crystallization, which provides the advanced intermediate VI in a yield that is acceptable for industrial production, approximately 80 to 90%.

This crystallization can be carried out from a polar protic organic solvent, preferably from lower $C_1$-$C_5$ alcohols, e.g. from ethyl alcohol.

In the procedure of the present invention 4-cyanophenyl aniline reacts with bromoacetic acid. Use of this different reagent results in a substantially higher yield, approximately 85-90%, as compared to 49% in the case of the reaction with chloroacetic acid. This will probably be caused by higher capability of the bromide ion to leave in nucleophilic reactions as compared to the chloride anion, which is significantly reflected in the reaction yield in the case of a reaction of 4-chloroacetic or 4-bromoacetic acid, resp., with a relatively weak nucleophile such as 4-cyanoaniline.

The whole manufacturing procedure will enable industrially feasible production of dabigatran. Substance VI produced in the above mentioned way can be further processed by the procedure according to WO 9837075.

In the next stage acidic hydrolysis of the nitrile function of compound VI and a reaction with ammonium carbonate producing the substance of formula VII is carried out.

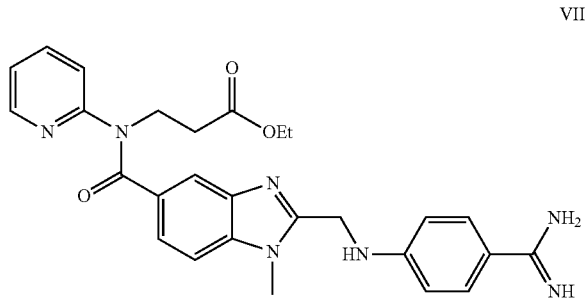 [SMILES: CCOC(=O)CCN(C(=O)c1ccc2c(c1)nc(CNc1ccc(C(=N)N)cc1)n2C)c1ccccn1]

The use of the entering substance VI in the oxalate form in accordance with the present invention produces compound VII in the hydrochloride form. This approach has a considerable purifying effect yielding the intermediate product VII with a high purity. The last stage is a reaction of intermediate VII with hexyl chloroformate producing dabigatran. The procedure in accordance with the present invention enables production of a high-quality product with a low content of impurities and a relatively high yield. The production of intermediates III and VI in the form of salts significantly simplifies the purifying operations during the manufacture of dabigatran; the chromatographic purification mentioned in WO 9837075 cannot be used in the industrial scale. This procedure will considerably increase the yield of the process. The reduction of the nitro group of substance III with the dithionite instead of the previously described catalytic hydrogenation with high demands on technology and material represents a substantial simplification and will positively influence the economy of the whole process.

The invention is further demonstrated in the following examples:

EXAMPLE 1

Preparation of ethyl 3-[[4-(methylamino)-3-nitrobenzoyl](pyridin-2-yl)amino]propanoate hydrochloride (III)

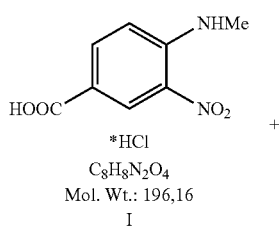

*HCl
$C_8H_8N_2O_4$
Mol. Wt.: 196,16
I

-continued

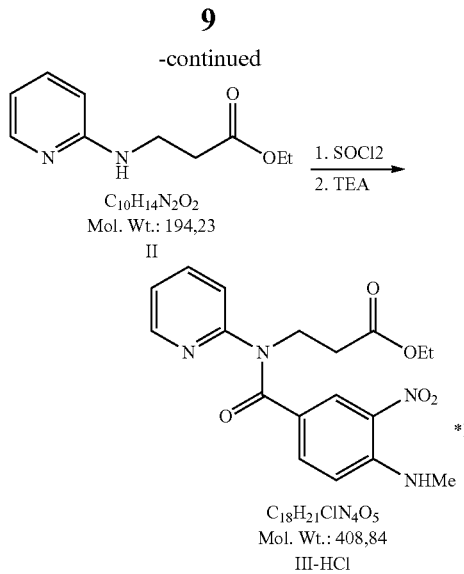

Ingredients:
Intermediate I: 100 g-0.51 mol
Intermediate II: 94 g-0.48 mol
Thionyl chloride: 850 ml
Dry triethylamine: 99 ml
Dimethyl formamide (dry): 4 ml
THF: 650 ml
Chloroform: 500 ml 850 ml of thionyl chloride and 4 ml of dry DMF were added to 100 g of substance I under inert atmosphere. The mixture was brought to boil. During that substance I got dissolved in several minutes and produced a dark brown solution. Then, the solution was refluxed for another 40-45 minutes. After that, excessive thionyl chloride was distilled off. To the brown residue 200 ml of dried toluene were added under inert atmosphere and the toluene was removed by distillation. This operation was repeated once again. The obtained brown crystalline residue was dissolved in dry THF (600 ml; under inert atmosphere) at an increased temperature.

After cooling of the solution of acid chloride I to the temperature of 40° C. dry triethylamine was added. To this solution a solution of substance II in dry THF (50 ml) was added dropwise. The time of dripping was 15 minutes. During the adding of substance II the reaction mixture was cooled in a water bath. This was accompanied by the temperature drop to 30° C. Then, the reaction mixture was stirred without heating for 2 hours. After sucking off triethylamine hydrochloride THF was evaporated. The evaporation residue was dissolved in 500 ml of chloroform and shaken with water. The separated organic layer was shaken with 2 M HCl and then with water.

The organic layer was dried with sodium sulphate and chloroform was evaporated.

Yield:
Crude product: 200 g (96%); HPLC: 88.2%; brown honey
The hydrochloride was prepared from this substance.

Preparation of the Hydrochloride

EtAc: 850 ml
HCl/Et$_2$O
The crude product was dissolved in 850 ml of ETAC at the laboratory temperature. 95 ml of a solution of HCl in Et$_2$O were added slowly to the solution dropwise under intensive stirring. During the stirring a yellow precipitate separates. After cooling in a fridge it was filtered off and dried (at the laboratory temperature overnight, then in vacuum at 55-75° C., then in vacuum without heating over the weekend (the weight remained already the same).

Yield:
Crude hydrochloride: 161.3 g (77.4%); HPLC: 93.3%

Crystallization of the Hydrochloride

The crude hydrochloride was crystallized from a mixture of denatured non-dried ethanol with acetonitrile 9:1.

Yield:
Crystallized hydrochloride: 120.2 g (61.6%); HPLC: 99.3%

EXAMPLE 2

Preparation of ethyl 3-[[3-amino-4-(methylamino)benzoyl](pyridin-2-yl)amino]-propanoate (IV)

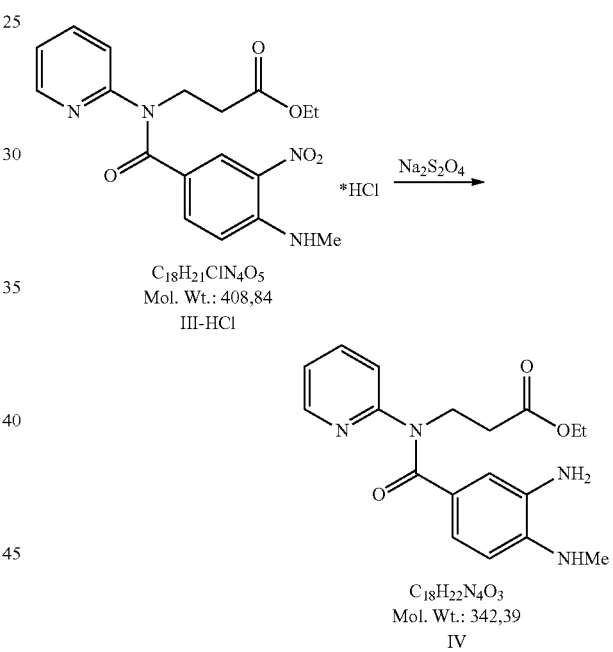

Ingredients
Intermediate III: 120 g-0.29 mol
Sodium dithionite: 246 g-1.2 mol
Ethanol: 750 ml
Ethyl acetate: 600 ml Substance III was put into 1500 ml of the ethanol—water mixture 1:1 and heated up to 50° C. This way a solution was created to which solid sodium dithionite was added quickly and under intensive stirring. After the starting substance has reacted the reaction mixture was concentrated in a vacuum evaporator. After separation of oil the concentration was completed and the product was extracted with ethyl acetate. After its drying with sodium sulphate the solvent is evaporated. The product is obtained as a brown, very viscous liquid.

Yield: 82 g (81.3%); HPLC: 95%

EXAMPLE 3

3.2.3 Preparation of [(4-cyanophenyl)amino]acetic acid (V)

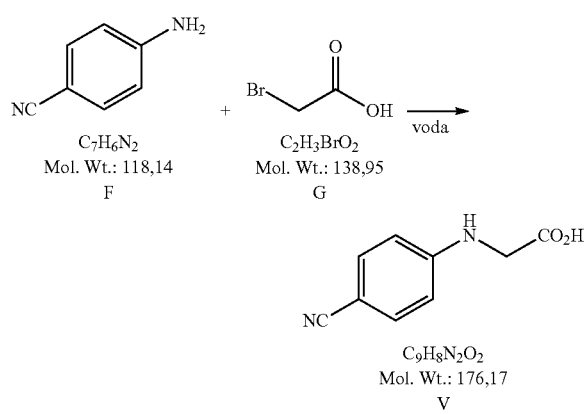

Ingredients
F: 90 g-0.75 mol
G: 211.7 g-1.5 mol
Sodium bicarbonate: 35 g, 0.42 mol The starting substances F and G were mixed in 1250 ml of water and this suspension was inserted into a bath heated up to 100-110° C. After three hours of heating the reaction container was removed from the bath, cooled in the fridge and the separated substance was sucked off. The substance was dried in a vacuum drier at the temperature of 100° C.

Yield:
Crude product: 122 g (92.8%), HPLC: 97%

The crude product was purified by conversion to the sodium salt and re-acidification using an aqueous solution of sodium bicarbonate. The acid was released by means of diluted hydrochloric acid (1:1). After sucking off and washing with water the product was dried in a vacuum drier (105° C.).

Yield:
Purified product: 115 g (88%), HPLC: 99.1%, water content: 0.13%; sulphate ash: 1.8%

EXAMPLE 4

Preparation of 3-([2-[(4-cyanophenyl amino)-methyl]-1-methyl-1H-benzimidazole-5-carbonyl]-pyridin-2-yl-amino)ethyl propionate oxalate (VI)

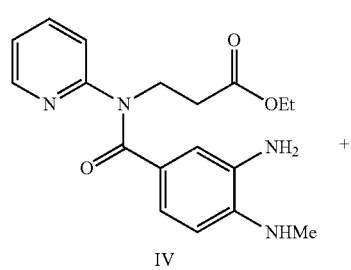

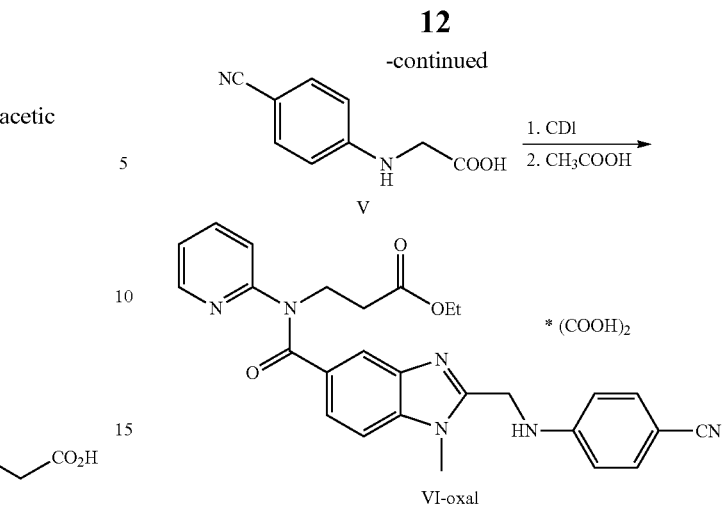

Ingredients
Intermediate IV: 82.5 g-0.24 mol
Intermediate V: 46.4 g-0.26 mol
1,1'-carbonyldiimidazole (CDI): 42.2 g-0.26 mol Procedure Substance V and 1,1'-carbonyldiimidazole are put into a flask blown with an inert gas. 2000 ml of dry THF are added and the mixture is boiled under a reflux condenser with a calcium-chloride tube for 40 minutes. After 40 minutes a solution of substance IV in 330 ml of dry THF is added to the mixture and the mixture is boiled for another 5 hours. After expiration of this time period the reaction mixture is slightly cooled and THF is removed by distillation in vacuum.

1000 ml of glacial acetic acid are added to the honey-like brown residue and the resulting solution is boiled for 1 hour. The acid is distilled off and the produced residue is dissolved in dichloromethane (850 ml) and shaken with water. The separated organic layer is dried with sodium sulphate and the solvent is evaporated. A dark brown honey-like residue is obtained.

Yield:
119 g (92% as the acetate); HPLC: 82%

Preparation of the Oxalate of Substance VI

The crude isolate (119 g) is dissolved in 650 ml of ETAC under boiling. The solution is cooled to the laboratory temperature and a solution of oxalic acid dihydrate (27.1 g) in 400 ml of ETAC is added dropwise under intensive stirring. A light beige substance separates quickly. The crystals are sucked off, washed with ethanol and dried.

Crude oxalate yield: 102 g (70%); HPLC: 90.2%

Crystallization of the Crude Oxalate of Substance VI 101 g of the crude product are dissolved in 4100 ml of ethanol under boiling. The solution is cooled in a water bath under simultaneous stirring. The crystal suspension is cooled in a fridge and the crystals are sucked off.

Yield of the crystallized oxalate: 82.5 g (57.2%); HPLC: 97.8%

The invention claimed is:

1. A method for the production of dabigatran of formula VIII

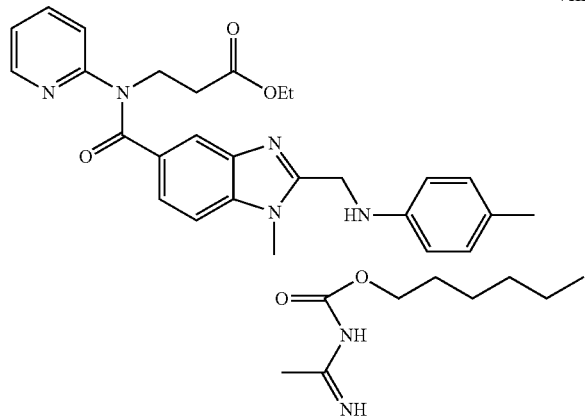

by reaction of 4-ethylamino-3-nitrobenzoic acid chloride with ethyl-3-(pyridin-2-ylamino)propanoate, reduction of the nitro group, subsequent reaction with [(4-cyanophenyl)amino]acetic acid, hydrolysis and reaction with ammonium carbonate and conversion to dabigatran by reaction with hexyl chloroformate, wherein the product of the reaction of 4-ethylamino-3-nitrobenzoic acid chloride with ethyl-3-(pyridin-2-ylamino)propanoate is converted to the hydrochloride using a hydrogen chloride solution to produce the compound of formula III-HCl

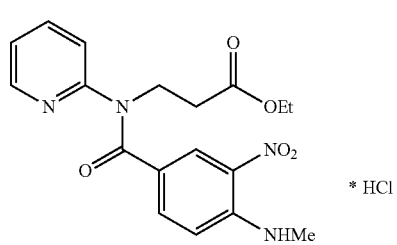

the nitro group of which is reduced by reaction with sodium dithionite and the resulting compound of formula IV

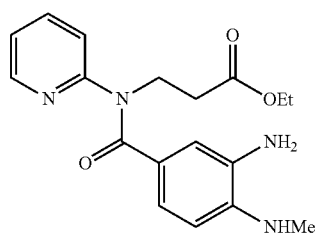

is subjected to reaction with [(4-cyanophenyl)amino]acetic acid of formula V and oxalic acid, the product of this reaction of formula VI-oxal

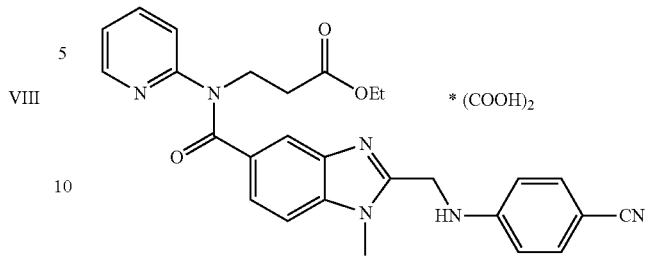

is then subjected to hydrolysis and reaction with ammonium carbonate to produce the intermediate of formula VII-HCl,

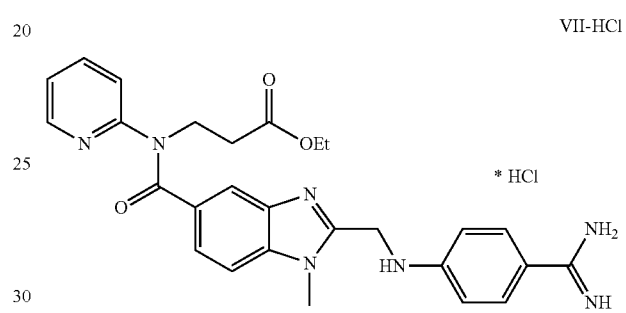

which is then converted to dabigatran by reaction with hexyl chloroformate.

2. The method according to claim 1, wherein 4-methylamino-3-nitrobenzoic acid chloride is reacted with ethyl-3-(pyridin-2-ylamino)propanoate in the presence of a base.

3. The method according to claim 1, wherein the product of the reaction of 4-ethylamino-3-nitrobenzoic acid chloride with ethyl-3-(pyridin-2-ylamino)propanoate in the base form is converted to the hydrochloride using a solution of hydrogen chloride in an organic solvent selected from $C_3$-$C_6$ ethers, ketones, esters and $C_1$-$C_5$ alcohols.

4. The method according to claim 1, wherein the product of the reaction of 4-ethylamino-3-nitrobenzoic acid chloride with ethyl-3-(pyridin-2-ylamino)propanoate in the base form is converted to the hydrochloride using a solution of hydrogen chloride in a solvent selected from diethylether, ethanol, ethyl acetate and acetone.

5. The method according to claim 1, wherein the product of the reaction of 4-ethylamino-3-nitrobenzoic acid chloride with ethyl-3-(pyridin-2-ylamino)propanoate in the base form is converted to the hydrochloride using a solution of hydrogen chloride in diethylether.

6. The method according to claim 2 wherein an organic or inorganic base is used.

7. The method according to claim 2 wherein an organic or inorganic base selected from amines, alcoholates, alkali hydroxides, phosphates and carbonates is used.

8. The method according to claim 2 wherein triethylamine is used as the base.

9. The method according to claim 2 wherein the obtained substance of formula III-HCl is purified by crystallization.

10. The method according to claim 2 wherein the obtained substance of formula III-HCl is purified by crystallization from an ethanol-acetonitrile mixture.

11. The method according to claim 1, wherein the reaction of the compound of formula III-HCl with sodium dithionite is performed in an ethanol-water solvent mixture.

12. The method according to claim 1, wherein the anhydrous form or one of the hydrates of oxalic acid is used.

13. The method according to claim 12, wherein the product is purified by crystallization.

14. The method according to claim 13, wherein the product is purified by crystallization using a solvent selected from ethanol and ethyl acetate.

15. The method for the manufacture of dabigatran according to claim 1, wherein the reaction of the 4-methylamino-3-nitrobenzoic acid chloride with ethyl-3-(pyridin-2-ylamino)propanoate is performed in the presence of a base at a temperature of 40-120° C. and the product is then converted to the hydrochloride using a hydrogen chloride solution to produce the compound of formula III-HCl.

16. The method for the manufacture of dabigatran according to claim 1, wherein the reaction of the compound of formula III-HCl with sodium dithionite producing the compound of formula IV is performed at a temperature of 20-100° C.

17. The method for the manufacture of dabigatran according to claim 1, wherein the reaction of the compound of formula IV with 4-cyanophenylglycine and oxalic acid is performed at a temperature of 40-120° C. to produce the compound of formula VI-oxal.

18. The method according to claim 1, wherein [(4-cyanophenyl)amino]acetic acid of formula V

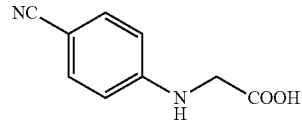

is obtained by reacting 4-cyanoaniline with bromoacetic acid.

* * * * *